(12) United States Patent
Fenske et al.

(10) Patent No.: US 6,267,836 B1
(45) Date of Patent: Jul. 31, 2001

(54) METHOD OF MANUFACTURING A TAPE TAB HAVING A ROUNDED USER'S END

(75) Inventors: Wilfried Horst Fenske, Bad Munster/Eifel; Christoph Johann Schmitz, Euskirchen-Stotzheim, both of (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 08/687,412

(22) PCT Filed: Feb. 3, 1995

(86) PCT No.: PCT/US95/01429

§ 371 Date: Apr. 28, 1998

§ 102(e) Date: Apr. 28, 1998

(87) PCT Pub. No.: WO95/20930

PCT Pub. Date: Aug. 10, 1995

(30) Foreign Application Priority Data

Feb. 4, 1994 (EP) .................................................. 94101673

(51) Int. Cl.[7] .............................. B32B 31/00; A61F 13/15
(52) U.S. Cl. ......................... 156/204; 156/211; 156/227; 156/252; 156/257; 156/268; 156/270; 428/99; 428/121; 428/192; 428/41; 604/385.11; 604/390

(58) Field of Search ..................................... 156/204, 211, 156/227, 256, 252, 257, 268, 270; 604/385.01, 385.11, 389, 390; 428/99, 121, 192, 41

(56) References Cited

U.S. PATENT DOCUMENTS

| | | | |
|---|---|---|---|
| 3,995,639 | * 12/1976 | Cheslow | 604/390 |
| 4,917,929 | 4/1990 | Heinecke | 428/41.4 |
| 5,147,347 | 9/1992 | Huang et al. | 604/390 |
| 5,151,092 | 9/1992 | Buell et al. | 604/385.3 |
| 5,242,436 | 9/1993 | Weil et al. | 604/384.29 |
| 5,312,387 | * 5/1994 | Rossini et al. | 604/389 |

OTHER PUBLICATIONS

International Search report dated Apr. 24, 1995 for PCT/US95/01429 filed Feb. 3, 1995.

* cited by examiner

*Primary Examiner*—Linda Gray
(74) *Attorney, Agent, or Firm*—Michael S. Kolodesh; David M. Weirich; Ken K. Patel

(57) ABSTRACT

A method of manufacturing tape tabs for use in disposable absorbent articles such as diapers. The method includes steps of cutting a unitary strip of material along parallel curved transverse lines to product tab shapes in the strip material having rounded corners, doubling over the strip material into itself to form a gripping area, and cutting the strip material along parallel cut lines which extend from the curved transverse cut lines to the longitudinal edge to form individual tape tabs.

15 Claims, 8 Drawing Sheets

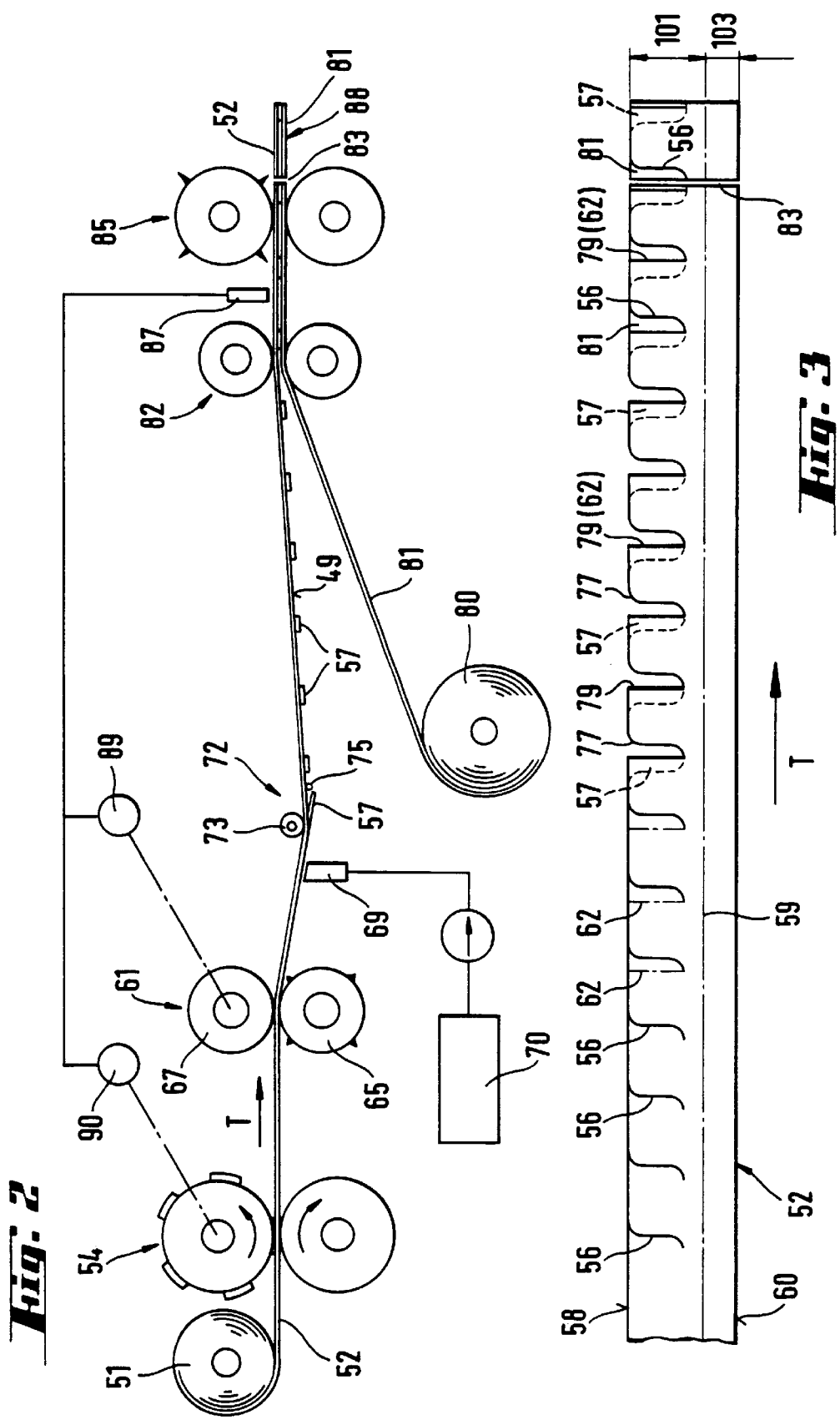

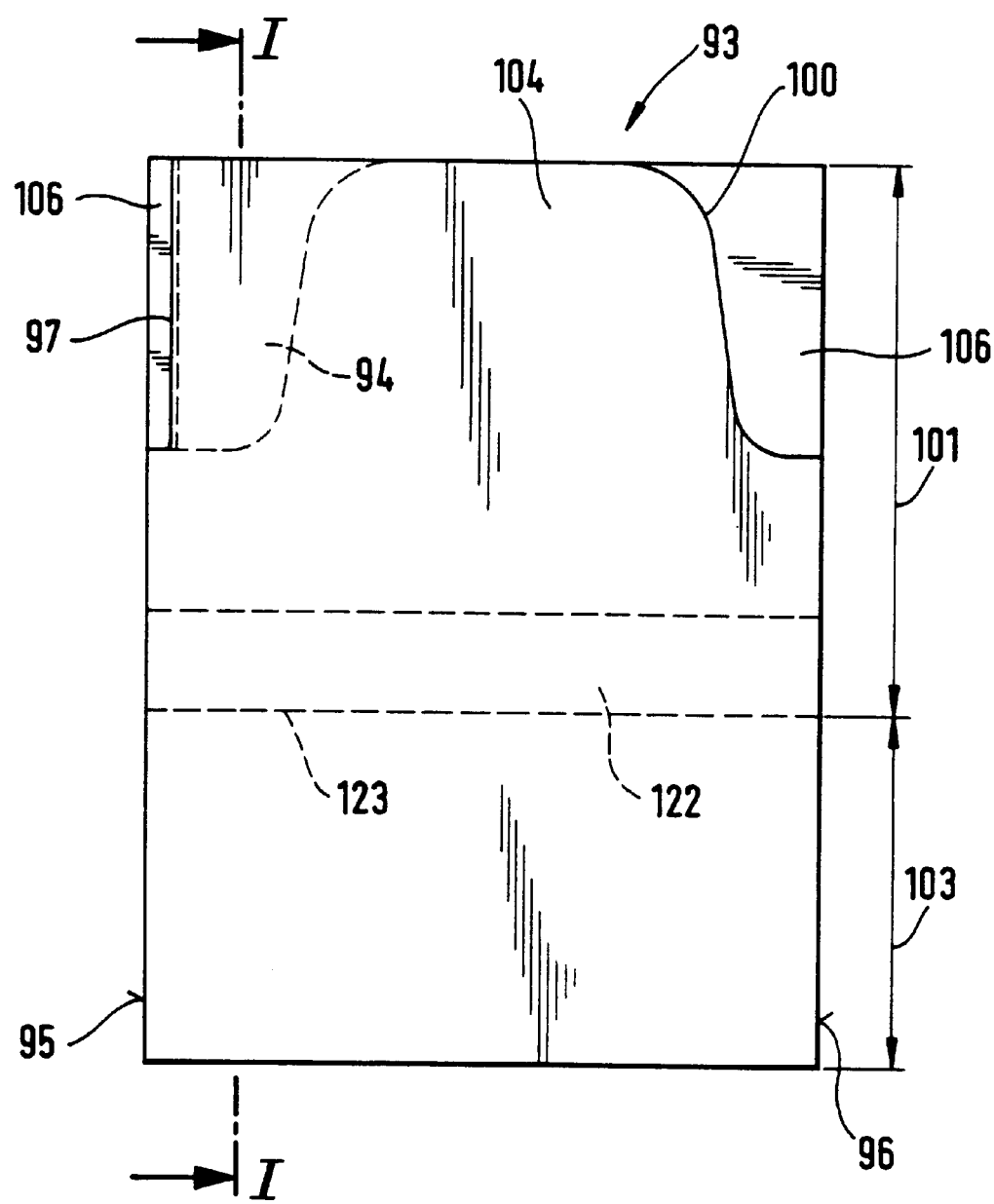

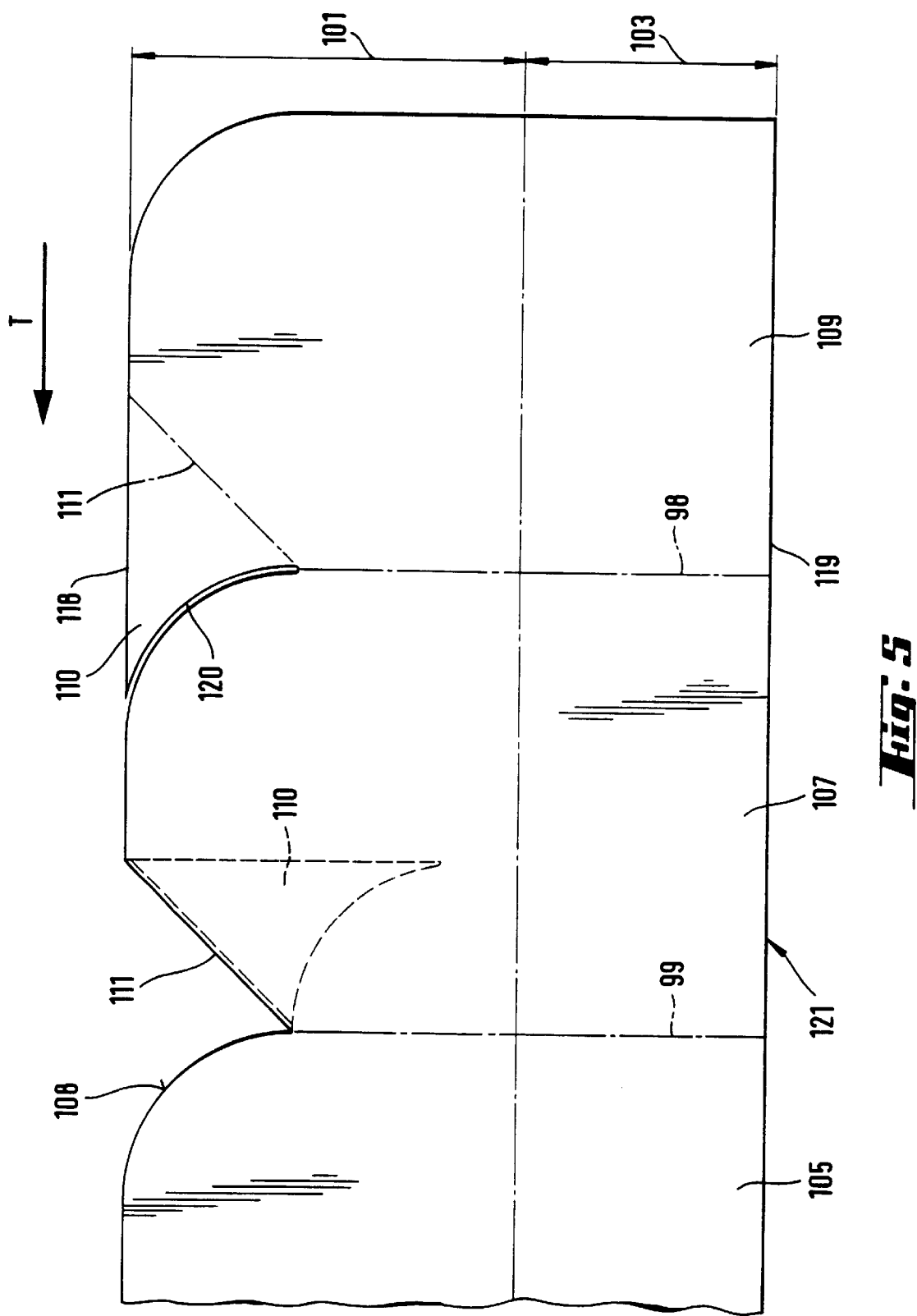

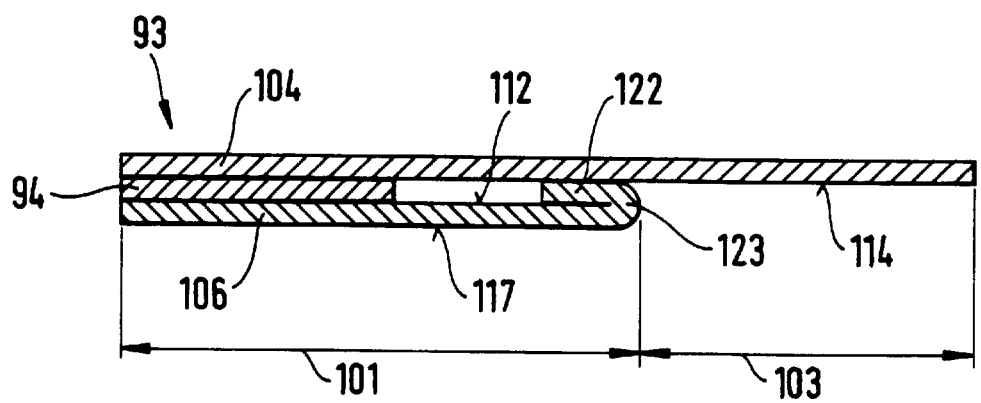
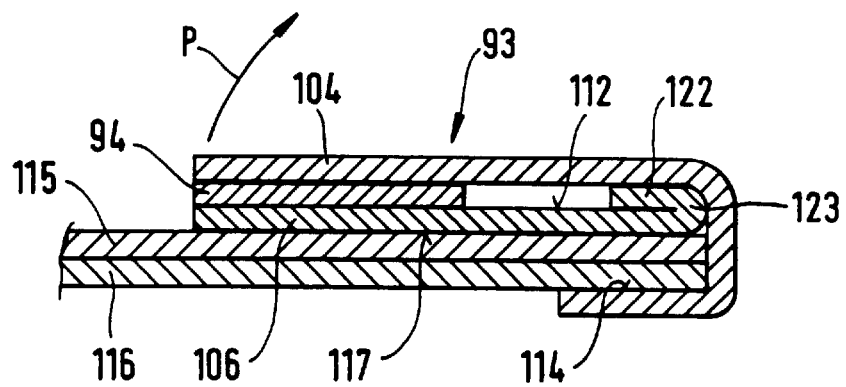

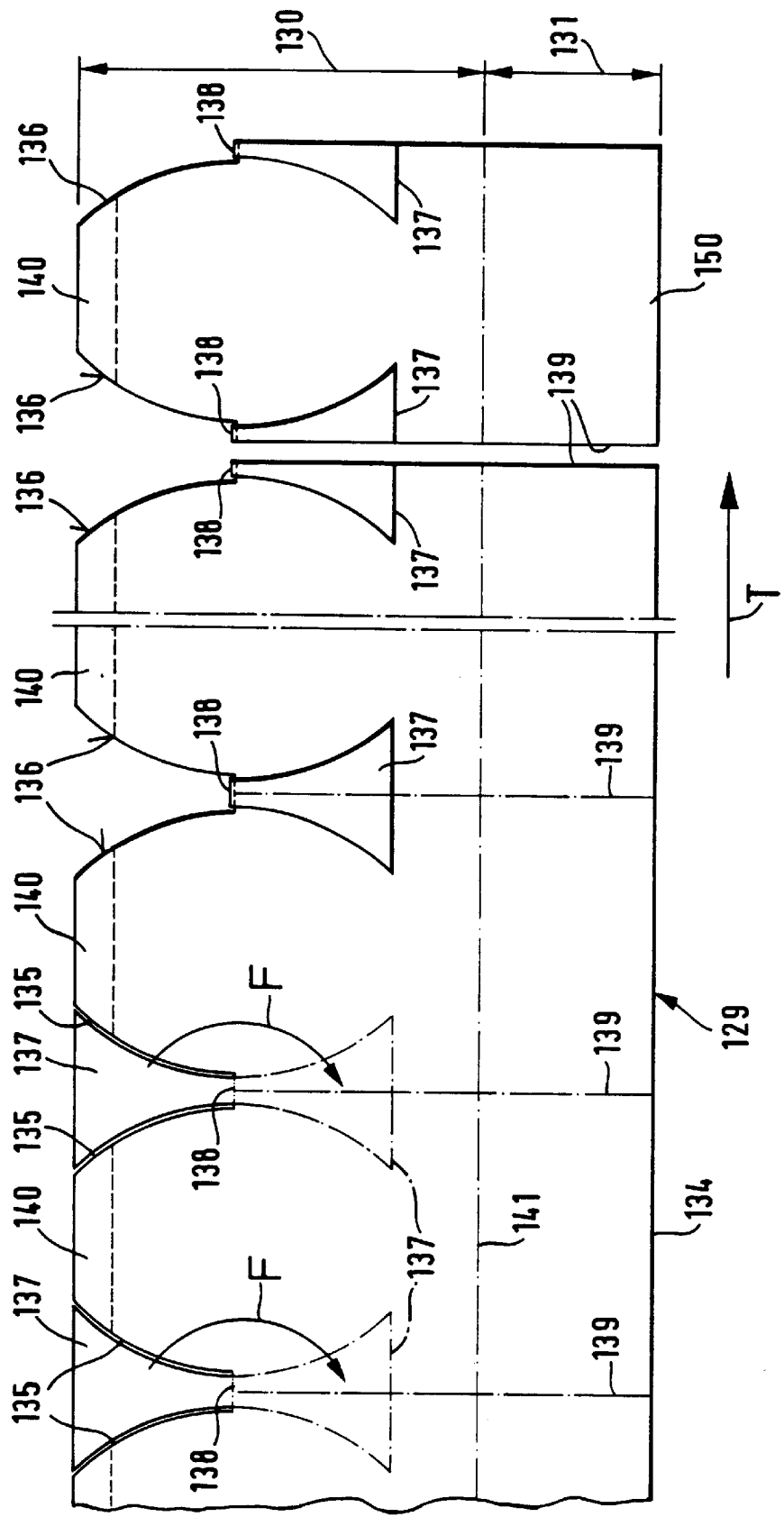

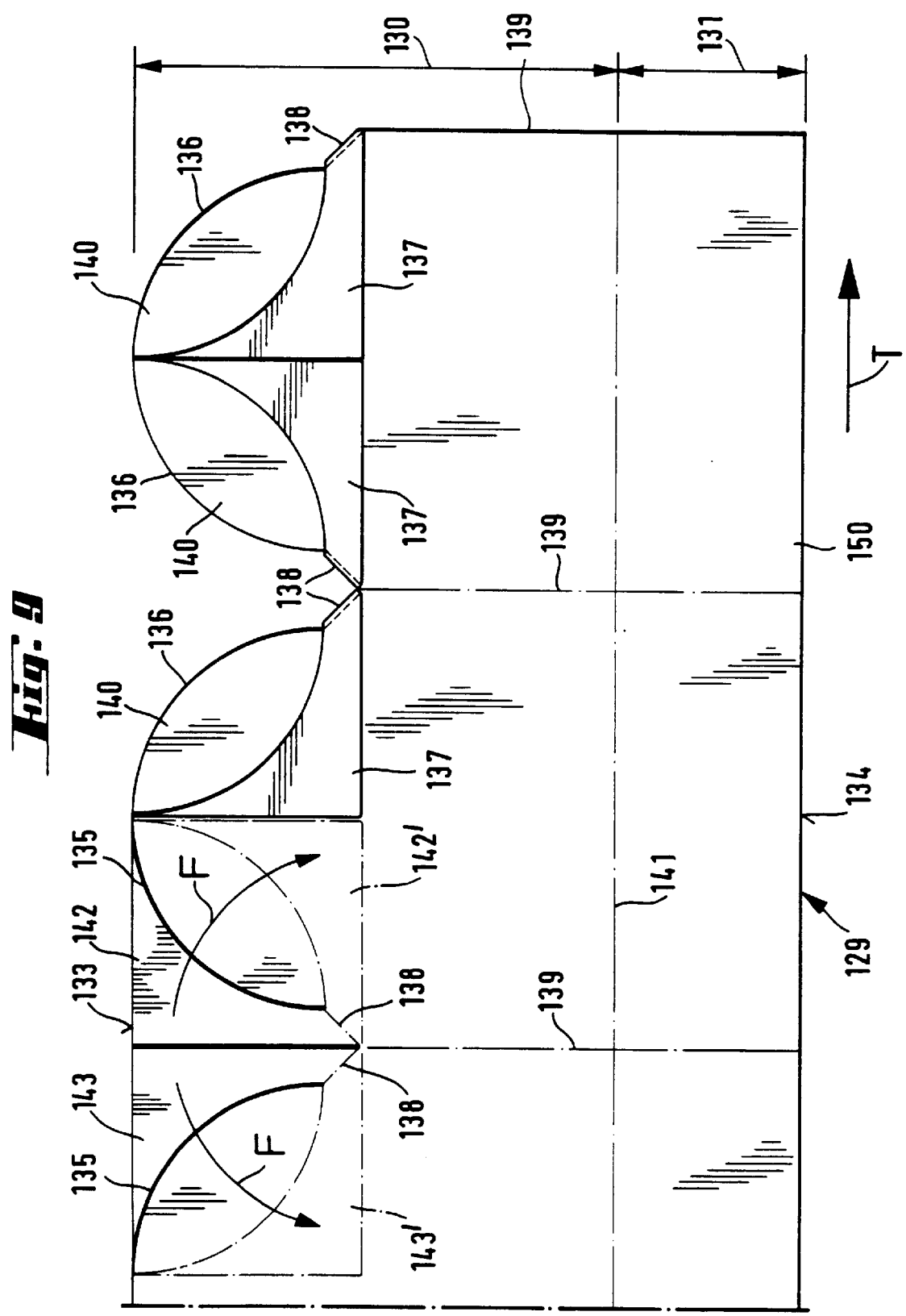

METHOD OF MANUFACTURING A TAPE TAB HAVING A ROUNDED USER'S END

FIELD OF THE INVENTION

The invention relates to a method of manufacturing a tape tab for use in an absorbent article, the tape tab having a rounded user's end.

The invention also relates to a tape tab for a disposable absorbent article and to a disposable absorbent article comprising such a tape tab.

BACKGROUND OF THE INVENTION

From EP-A-0 379 850, a method is known for producing a tape system from a unitary strip, the tapes having rounded user's ends. According to the method of the above patent application, a longitudinal unitary strip of material is coated with adhesive, such that a central adhesive-free zone is present. A number of parallel, transversely extending straight cut lines are made, running from both longitudinal sides of the unitary strip towards the longitudinal center line. Two sinusoidal, longitudinal cut lines, bridge the straight-line, transverse cuts on both sides of the longitudinal center line to form individual tape tabs which each have an adhesive-free, rounded user's end.

A disposable absorbent article having tapered tape tabs with rounded user gripping parts is known from EP-A-0 233 704. The tapes are cut from a single strip of elongated material, in such a way that no scrap is produced. This is achieved by cutting the strip along straight transverse cut lines, running from the longitudinal sides of the strip towards the center line, the cut lines on opposite sides of the longitudinal center line being displaced relative to one another by half a tape width. A single, sinusoidal cut-line extends in the length of the strip, along the longitudinal center line of the strip to form the rounded user's end on each tape tab.

A disposable absorbent article having a tape tab comprising a combined adhesive fastener and a tape fastener is known from EP-A-0 321 132. In this patent application a tape tab is shown having a doubled-over user's end and a fastening surface to which a patch of VELCRO material is attached. An additional adhesive patch on the fastening surface of the tape tab provides for a disposal means to maintain the diaper in a rolled up or folded disposal-configuration after use. Because the end parts of the tapes are doubled over, the end parts are rounded along the thickness of the tape, and provide user-friendly gripping parts.

It is an object of the invention to provide a tape tab having at its user's end a gripping part that allows easy handling by the user, and which comprises a reinforcement area.

It is again an object of the invention to provide a tape tab that is baby-friendly and which minimizes the chances of skin-irritation upon wearing.

It is a further object of the present invention to provide a method of producing tape tabs from a unitary strip of material, in which the scrap produced on cutting is minimized.

It is another object of the present invention, to provide a method of making a tape tab for use in a disposable absorbent article, the tape tab having a rounded user-end.

SUMMARY OF THE INVENTION

The method according to the invention is characterized by:

a. cutting a unitary strip of material along parallel, spaced apart curved transverse cut lines, wherein the unitary strip of material comprises two longitudinal edges, the transverse cut lines extending from a first longitudinal edge in the direction of the second longitudinal edge, each curved cut line forming the contour of a rounded corner of the user's end of a first tape tab and forming a side extension of the user's end of a second tape tab which is adjacent the first tape tab, b. doubling over of each side extension onto itself along a fold line to form the gripping parts, and c. cutting the unitary strip of material along further parallel cut lines which extend from the curved transverse cut lines to the second longitudinal edge to form individual tape tabs.

By cutting the tapes along the curved cut lines, the material that is cut off the corner of one tape tab, remains attached to the neighboring tape tab to form a side extension of the neighboring tape tab. By folding back the side extension onto itself, a reinforced user's end is formed having a rounded corner. When the tape tabs are attached to an absorbent article, the rounded corner is closest to the waist edge of the absorbent article. The rounded corner reduces the chance of injury to the baby wearing the absorbent article, and can be easily gripped by the mother at the lower, doubled-over corner. The tape tabs can be adhesive tape tabs, mechanical tape tabs, or combinations thereof.

Adhesive tape tabs are attached at their manufacturer's end to an absorbent article, the user's end of the tape tabs, before use of the absorbent article, being glued to a release surface. An adhesive tape tab according to the present invention can be easily detached from the release surface, for application of the article to a baby, by lifting the doubled over user's-end with a finger tip and pealing back the tape. The doubled-over user's end does not become attached to the backsheet of the absorbent article upon application of the article to a baby, and forms a reinforced gripping part which can easily be lifted. Hence the tape tab according to the invention also provides for easy detachment of the tapes on removal of the absorbent article from the baby after use or for adjustment and reattachment of the tape tabs during use.

No scrap material is produced by the method of manufacturing tape tabs according to the invention.

In an embodiment or the method according to the invention, curved transverse cut lines are formed along a longitudinal edge of the unitary strip, to form cut-out sections. By folding over of one cut-out section, rounded corners of each time two neighboring tape tabs are formed. The tape tabs made according to this embodiment have two rounded corners at their user's end.

In a further embodiment of the method according to the invention, one surface of the unitary strip of material is provided with an adhesive and is covered with a unitary release strip. The combined unitary strip of material and the release strip are cut along transverse cut lines to form individual, composite tape tabs. The composite tape tabs each comprise a fastening member and a release member. The length of the tape tabs corresponds to the width of the unitary strip of material from which the tape tabs are cut. In one embodiment, the release strip is of equal width as the unitary strip of material, such that for a composite tape tab the fastening member and the release member are equal in length.

The attachment of the tape tabs to an absorbent article by the manufacturer can occur in several ways.

In case the tape tabs are comprised of a single fastening member only and do not comprise a release member, the manufacturer's end of the tape tabs can be directly attached to the backsheet of the absorbent article. Prior to attachment of these tape tabs, the absorbent article can have been provided with a reinforcement material in the anchoring regions in which the manufacturer's ends of the tape tabs are to be attached. The diaper can in such a case also comprise a release surface which is attached to the topsheet and to which the user's end of the tape tabs can be applied on assembly of the diaper by the manufacturer.

The tape tabs can comprise near their user's end a pressure sensitive adhesive or a mechanical fastening means of the type described in U.S. Pat. No. 5,180,534, U.S. Pat. No. 5,058,247 and U.S. Pat. No. 5,116,563, which fastening means easily detaches from the reinforcement material that is attached to the topsheet. At the manufacturer's end, the tape tabs can be provided with a strong adhesive which permanently attaches to the reinforcement material of the absorbent article.

In case the tape tabs are comprised of composite tape tabs, the release member of the tape tabs can be permanently fastened to the absorbent article by means of a relatively aggressive adhesive.

In this case, the reinforcement material in the anchoring regions on the absorbent article, is formed by the release member and need not be pre-applied. In case the release member is shorter in length than the fastening member, the fastening member of the composite tape tabs is at the manufacturer's end fastened directly to the backsheet of the absorbent article. In a further embodiment of a method according to the invention, the fold line of the side extensions of the tape tabs comprises a curved section located between two straight short fold lines on either side of the curved section. The curved section of the fold line is cut through, while the straight parts of the fold line are creased or perforated. By folding-over the side extension of each tape tab along the straight parts of the fold line, the tapes are at the user's end provided with two rounded corners instead of one rounded corner and one angled corner.

BRIEF DESCRIPTION OF THE DRAWINGS

The invention will be explained in detail with reference to the accompanying drawings. In the drawings:

FIG. 2 shows a schematic side view of a method for manufacturing tape tabs according to the invention, FIG. 3 shows a top view of a unitary strip of material used in the method of FIG. 2, FIG. 4 shows a plan view of a composite tape tab according to the invention, FIG. 5 shows a plan view of three neighboring tape tabs according to the invention before the formation of individual tape tabs, FIG. 6 shows a cross sectional view of the composite tape tab of FIG. 4 along the line I—I, FIG. 7 shows a cross-sectional view of the composite tape tab of FIG. 4 wherein the manufacturer's end of the tape tab is attached to an absorbent article, FIG. 8 shows a plan view of three neighboring tape tabs and an individual tape tab having two rounded corners at the user's end, FIGS. 9 and 10 show a plan view of three neighboring tape tabs having two rounded corners at the user's end and comprising 45°-fold lines.

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 1, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, diaper holders and liners, and the like.

Figure 1:
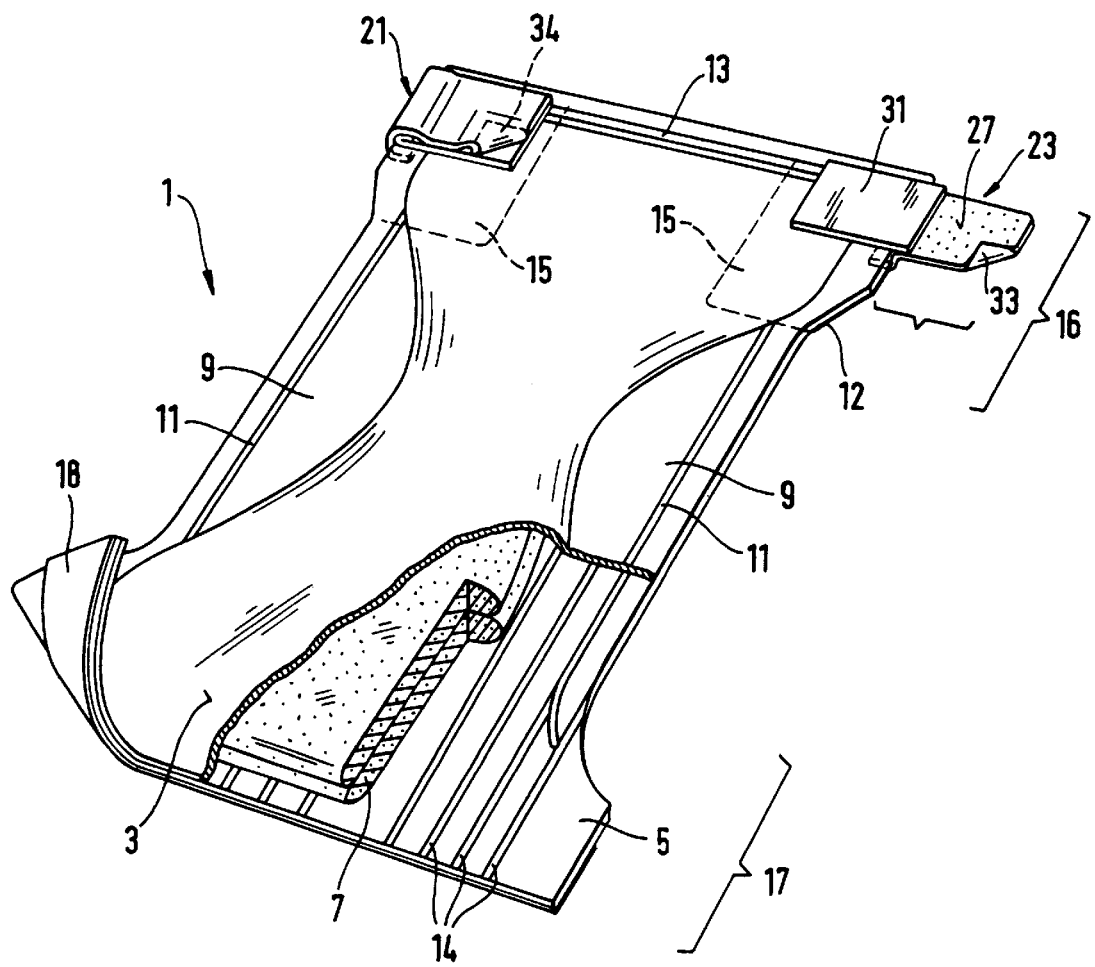
FIG. 1 shows a partially cut-away plan view of an absorbent article comprising a pair of tape tabs according to the invention.

FIG. 1 is a plan view of the diaper 1 of the present invention in its flat-out, state (i.e., with elastic induced contraction pulled out) with portions of the structure being cut-away to more clearly show the construction of the diaper 1 and with the portion of the diaper 1 which faces or contacts the wearer, the inner surface, oriented towards the viewer. As shown in FIG. 1, the diaper 1 preferably comprises a liquid-permeable topsheet 3; a liquid impervious backsheet 5 joined with the topsheet; an absorbent core 7 positioned between the topsheet 3 and the backsheet 5; side panels 9; elasticized stand-up leg cuffs not shown in FIG. 1 an elastic waist feature 13 and a fastening system 21, 23.

FIG. 1 shows a preferred embodiment of the diaper 1 in which the topsheet 3 and the backsheet 5 have length and width dimensions generally larger than those of the absorbent core 7. The topsheet 3 and the backsheet 5 extend beyond the edges of the absorbent core 7 to thereby form the periphery 12 of the diaper 1. While the topsheet, the backsheet, and the absorbent core may be assembled in a variety of well known configurations, preferred diaper configurations are described generally in U.S. Pat. No. 3,860,003 entitled "Contractable Side Portions for Disposable Diaper" which issued to Kenneth B. Buell on Jan. 14, 1975; and U.S. patent application Ser. No. 07/715,152 (abandoned), "Absorbent Article With Dynamic Elastic Waist Feature Having A Predisposed Resilient Flexural Hinge", Kenneth B. Buell et al. filed Jun. 13, 1991; each of which is incorporated herein by reference.

The absorbent core 7 may be any absorbent means which is generally compressible, conformable, non-irritating to the wearer's skin, and capable of absorbing and retaining liquids such as urine and other certain body exudates. The absorbent core 7 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic; tissue including tissue wraps and tissue laminates; absorbent foams; absorbent sponges; superabsorbent polymers; absorbent gelling materials; or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 7 should, however, be compatible with the design loading and the intended use of the diaper 1. Further, the size and absorbent capacity of the absorbent core 7 may be varied to accommodate wearers ranging from infants through adults. Exemplary absorbent structures for use as the absorbent core 7 are described in U.S. Pat. No. 4,610,678 entitled "High-Density Absorbent Structures" issued to et al. on Sep. 9, 1986; U.S. Pat. No. 4,673,402 entitled "Absorbent Articles With Dual Layered Cores" issued to Weisman et al. on Jun. 16, 1987; U.S. Pat. No. 4,888,231 entitled "Absorbent Core Having A Dusting Layer" issued to Weisman on Dec. 19, 1989; and U.S. Pat. No. 4,834,735, entitled "High Density Absorbent Members Having Lower Density and Lower Basis Weight Acquisition Zones", issued to Alemany et al. on May 30, 1989. Each of these patents are incorporated herein by reference.

The backsheet 5 is positioned adjacent the garment surface of the absorbent core 7 and is preferably joined thereto by attachment means such as glue lines 14. The backsheet 5 may be secured to the absorbent core 7 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste Containment Garment", which issued to Minetola et al. on Mar. 4, 1986 more preferably several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these Patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 5 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 5 prevents the exudates absorbed and contained in the absorbent core 7 from wetting articles which contact the diaper 1 such as and undergarments. The backsheet 5 may thus comprise a woven or material, polymeric films such as thermoplastic films of polyethene or polypropylene or, or composite materials such as a film-coated nonwoven material. Preferably, the backsheet is a film having a thickness of from about 0.012 mm (0.5 mil) to about 0.051 mm (2.0 mils). Particularly preferred materials for the backsheet include RR821 blown films and RR5475 cast films as manufactured by Tredegar Industries, Inc. of Terre Haute, Ind. The backsheet 5 is preferably embossed and/or matte finished to provide a more clothlike appearance. Further, the backsheet 5 may permit vapors to escape from the absorbent core 7 (i.e. breathable,) while still preventing exudates from passing through the backsheet 5.

The topsheet 3 is positioned adjacent the body surface of the absorbent core 7 and is preferably joined thereto and to the backsheet 5 by attachment means (not shown) such as those well known in the art. Suitable attachment means are described with respect to joining the backsheet 5 to the absorbent core 7. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the topsheet 3 and the backsheet 5 are joined directly to each other in the diaper periphery 12 and are indirectly joined together by directly joining them to the absorbent core 7 by the attachment means (not shown).

The topsheet 3 is compliant, soft feeling, and non-irritating to the wearer's skin. Further, the topsheet 3 is liquid pervious permitting liquids (e.g., urine) to readily penetrate through its thickness A suitable topsheet may be manufactured from a wide range of materials, such as porous foams; reticulated foams; apertured plastic films; or woven or nonwoven webs of natural (e.g., wood or cotton), synthetic (e.g., polyester or polypropylene or), or a combination of natural and synthetic. Preferably, the topsheet 3 is made of a hydrophobic material to isolate the wearer's skin from liquids contained in the absorbent core 7. There are a number of manufacturing techniques which may be used to manufacture the topsheet 3. For example, the topsheet 3 may be a nonwoven web of, spunbonded, carded, wet-laid, meltblown, hydroentangled, combinations of the above, or the like. A preferred topsheet is carded and thermally bonded by means well known to those skilled in the fabrics art. A preferred topsheet comprises a web of staple length polypropylene such as is manufactured by Veratec, Inc., a Division of International Paper Company, of Walpole, Mass. under the designation P-8.

The diaper 1 preferably further comprises elasticized leg cuffs 11 for providing improved containment of liquids and other body exudates. Each elasticized leg cuff 11 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff.

The Diaper 1 preferably further comprises an elastic waist feature 13 that provides improved fit and containment. The elastic waist feature 13 is that portion or zone of the diaper 1 which is intended to expand and contract to dynamically fit the wearer's waist. The elastic waist feature 13 at least extends longitudinally outwardly from at least one of the waist edges of the absorbent core 7 and generally forms at least a portion of the end edge of the diaper 1. Disposable diapers are generally constructed so as to have two elastic waist features, one positioned in the first waist region 16 and one positioned in the second waist region 17, although diapers can be constructed with a single elastic waist feature. Further, while the elastic waist feature or any of its constituent elements can comprise a separate element affixed to the diaper 1, the elastic waist feature 13 is preferably constructed as an extension of other elements of the diaper such as the backsheet 5 or the topsheet 3, preferably both the backsheet 5 and the topsheet 3. The elasticized waistband 13 may be constructed in a number of different configurations including those described in U.S. Pat. No. 4,515,595 issued to Kievit et al. on May 7, 1985 and the above referenced U.S. patent application Ser. No. 07/715,152 (abandoned); each of these references being incorporated herein by reference.

In a preferred embodiment, the diaper also comprises elasticized side panels 15 disposed in the attachment areas of tabs 21, 23 and indicated in FIG. 1 by the broken lines. The elasticized side panels 15 provide an elastically extensible feature that provides a more comfortable and contouring fit by initially conformably fitting the diaper to the wearer and sustaining this fit throughout the time of wear well past when the diaper has been loaded with exudates since the elasticized side panels allow the sides of the diaper to expand and contract. The elasticized side panels 15 further provide more effective application of the diaper 1 since even if the diaper pulls one elasticized side panel by pulling of tape tabs 21, 23 farther than the other during application (asymmetrically), the diaper 1 will "self adjust" during wear. While the elasticized side panels 15 may be constructed in a number of configurations, examples of diapers with elasticized side panels positioned in the ears (ear flaps) of the diaper are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; and the hereinbefore referenced U.S. patent application Ser. No. 07/715,152 (abandoned); each of which are incorporated herein by reference.

The diaper 1 of FIG. 1 comprises in the waist region 16 two tape tabs 21, 23. The tape tabs each comprise a manufacturer's end which is attached to the backsheet of the diaper 1 in an anchoring zone. Tape tab 23 is shown in an extended position in which the adhesive fastening surface 27 of the user's end 32 of the tape tab 23 is facing upward. The manufacturers end of the tape tabs 21, 23 is adhesively affixed to the backsheet 5. As used herein, the user's end of the tape tabs 21, 23 refers to the part that can be gripped by a user of the absorbent article and that can be attached to an attachment zone of backsheet to put the diaper 1 on a baby. The manufacturers end of the tape tabs 21, 23 refers to the part that is permanently attached to an anchoring zone of the topsheet 3 or to an anchoring zone of the backsheet 5.

A reinforcement element 31 attaches the tape tabs 21, 23 to the an anchoring zone of the topsheet 3. The reinforcement element 31 provides a strengthening of the topsheet 3 in the anchoring regions and prevents the tapes from tearing off the topsheet 3 upon use. Preferably, the backsheet 3 is also provided with a reinforcement material in the anchoring zone. The reinforcement element 31 extends beyond the periphery 12 of the diaper and is attached to the adhesive fastening surface 27. Each tape tab 21, 23 comprises at its user's end 32 a side extension 33, 34. The side extensions 33, 34 of the tape tabs are doubled over onto the adhesive fastening surface 27 and are thereby prevented from unfolding. The doubled-over side extensions form reinforced gripping parts of the tape tabs 21, 23.

Upon application of the diaper to a baby, the user's ends of the tape tabs 21, 23 are attached to a landing zone of the backsheet that is located in the second waist region 17, either directly onto the backsheet 5 or onto a reinforced landing surface 18. The reinforced landing surface 18 can be formed by a single strip or by individual patches of polyethylene or polypropylene and can be located on the outward facing side of the backsheet 5 or can be located on the inward facing side thereof. The tape tabs can be released from the reinforced landing surface 18 without tearing of the backsheet and can be reapplied to the landing surface for re-adjustment of the diaper. The relationship between the surface texture of the reinforced landing surface and the adhesive properties of the tape tabs, have been described in U.S. Pat. No. 3,867,940, U.S. Pat. No. 4,210,144, GB-A-2 129 689, EP-B-0 080 647 and EP-B-0 286 030.

When the diaper 1 is placed on a baby, the doubled-over side extensions 33, 34 at the user's ends of the tape tabs are located underneath the outwardly facing surface of the tape tabs 21, 23. Hereby it is prevented that the baby suffers any discomfort from contact with the side extensions 33, 34. The positioning of the side extensions underneath the outwardly facing surface of the user's ends of the tape tabs, also helps in preventing the baby from loosening the tape tabs.

Before application of the diaper to the baby, the tape tabs 21, 23 are doubled over such that the adhesive fastening surface 27 is located on the reinforcement element 31, as is shown for tape tab 21 in FIG. 1. The outwardly-facing surface of the reinforcement element 31 is preferably smooth such that the adhesive fastening surface 27 of the user's end 32 easily detaches therefrom. The outer surface of the reinforcement element 31 may be treated with a release coating, such as for instance a silicone coating. The doubled-over side extensions 33, 34 of tape tabs 21, 23 allow the tapes to be easily lifted from the reinforcement element 31 or from the reinforced landing surface 18.

FIGS. 2 and 3 respectively show a schematic side view of a production line for manufacturing the tape tabs in accordance with the invention and the unitary strip of material from which the individual tape tabs are formed in said production line. From a supply roll 51, a unitary strip of material 52 is unwound in the direction of transport, which is indicated by the arrow T. The unitary strip of material 52 forms the fastening member for the tape tabs and is for instance formed of a plastic or paper backed material of a width of 6 cm and a thickness of 130 micrometers, preferably coated with a pressure or heat sensitive glue, such as supplied by 3M GmbH, Hansastr. 9, Neuss. The width of the strip 52 corresponds to the length of the finished tape tabs. Alternatively, the strip of material 52 is coated with glue on line, as shown in FIG. 2. The unitary strip of material passes a diecutter 54, which comprises an upper knife roll assembly, and a lower cylindrical roll acting as an anvil roll which is contacted by the knife roll. The diecutter 54 provides the strip 52 with a number of parallel, spaced apart, curved transverse cuts 56 as shown in FIG. 3, which extend from the longitudinal side 58 of the strip 52 in the direction of the second longitudinal side 60.

After passing through the die-cutter 54, the strip 52 passes through a creasing unit 61, in which the strip is provided with crease lines 62. The creasing unit comprises a lower roll 65 which is provided with a rim extending along the circumference of roll 65. The rim can be parallel to the axis of roll 65, or it can be skewed around a section of the surface of roll 65. Roll 65 is adjusted against roll 67 such that the rim has a clearance of generally about half the thickness of the strip 52. The rim on the lower roll 65 presses the strip 52 against the cylindrical surface of the upper roll 67, thereby forming crease- or fold lines 62 in strip 52.

When glue is applied to the strip 52 on-line, a layer of pressure sensitive adhesive, such as available from Findley Euro B.V., Rotkreuzweg 7, D-6380 Bad Homburg, is applied to the lower surface 49 of strip 52 via a glue nozzle 69. The layer of glue may comprise a spiral or other intermittent pattern, or can be applied as a continuous layer, for instance by means of slot coating. In the present embodiment, the adhesive is supplied to the nozzle from a storage tank 70. When a preglued strip 52 is used, the nozzle 69 and the storage tank 70 are not required.

In a folding unit 72, the side extensions 57 of the tape tabs are doubled over onto the lower surface 49 of the strip 52. The side extensions are formed by the areas of the strip 52 that are located between the fold lines 62 and the cut lines 56 near the longitudinal side 58 of the strip 52. The fastening surface of the strip 52 is comprised of the lower surface 49 of the strip 52 in FIG. 2. The user's ends 101 of the tape tabs 88 which are formed from the strip 52, are in this example located near the longitudinal side 58. The folding unit 72 comprises a roll 73, which strains the surface of the strip 52 by pressing the strip out of the plane of transport, preferably such that at roll 73, the strip 52 forms an obtuse angle. Thereby, the side extensions 57 are pressed out of the plane of the strip 52 and stand away from the plane of the strip. The uplifted side extensions 57 are caught behind a folding wire 75 which is located adjacent the lower surface of the strip 52 and which extends generally perpendicular to the plane of the drawing. Upon transporting the strip 52 past the folding wire 75, the side extensions 57 are folded onto the lower surface of the strip 52, and are held in position by the double layer of adhesive located between the lower surface of the strip 52 and the doubled over side extensions 57.

By folding over of the side extensions 57, the rounded corners 77 and the straight corners 79 of the tape tabs are formed. The strip 52 is after formation of the rounded corners 77 combined with a release strip 81, which is unwound from a supply roll 80. The release strip 81 can be of equal width as the user's end 101 of the strip 52, as is shown in FIGS. 6 and 7. The release strip can also be equal in width to the total width of the user's end 101 and the manufacturer's end 103 of the strip 52. In the nip 82, the release strip 81 is combined with the adhesive surface of the strip 52. At the final stage of the tape forming process, the strip 52 is cut in a cutting unit 85 along transverse cut lines 83 extending form the upper side 58 to the lower side 60 of both the strip 52 and the release strip 81, to form the individual composite tape tabs 88. The individual composite tape tabs comprise a fastening member and a release member. The fastening member is formed by the cut off parts of unitary strip of material 52. The release member is formed by the cut off parts of the release strip 81. The length of the tape tabs corresponds to the width of the strip 52.

The transverse cut lines 83 should ideally be located at a fixed position relative to the fold lines 62 of adjacent tape tab. In practice, the position of the transverse cut lines can be allowed to vary by a fraction of the distance between the rounded corner 56 of one tape tab and the fold line 62 of the neighboring tape tabs for instance by 1 or 2 mm. Displacement of the transverse cut lines 83, which are for instance caused by variations in the speed of the strip 52, can lead to cutting open of the fold lines 62 in the cutting unit 85. To minimize the variation in the position of the transverse cut lines 83, an optical detector 87, such as a photo diode or a Charge Coupled Device (CCD) is placed over the strip 52, upstream of the cutting unit 85, to measure the position of the rounded corners 56 or the position of straight-edge corners 79. The optical detector 87 can distinguish the boundary between the strip 52 and the release strip 81. The signal of the optical detector 87 is fed back to the servo drives 89 and 90, which drive the creasing unit 61 and the die-cutter 54. By controlling the speed of transport of the strip 52, the transverse cut lines 83 can be located at a position along the strip 52 which varies by not more than 1 to 2 mm.

FIG. 4 shows an embodiment of a composite tape tab 93 comprising an upper fastening member 104 and an underlying release member 106, which in this figure is only visible at upper left- and right hand corners of the tape tab 93. The composite tape tab 93 is similar to the tape tabs as formed in process as shown in FIGS. 2 and 3. The tape tab of FIG. 4 is the mirror image of the tape tabs which are formed according to the process of FIG. 2. In effect, for attachment to an absorbent article, two tape tabs are required which are mirror images with respect to one another. The tape tab 93 of FIG. 4 can be formed in the process as shown in FIGS. 2 and 3 by providing the transverse cuts 56 at the lower longitudinal side 60 of the strip 52.

Preferably the fastening member 104 of the composite tape tab 93, which fastening member is facing the viewer, is transparent, or semitransparent. The folded-over side extension 94 and the rounded corner 100 of the tape tab 93 result in a symmetrical appearance of the tape tab 93, even though the fold line 97 is straight and extends generally in the direction of the longitudinal sides 95, 96 of the tape tab 93. The symmetrical shape of the transparent or semi-transparent tape tab 93 is of advantage if the tape tab is fastened on a landing surface 18 on the backsheet of a diaper which is provided with optical fit guides. The optical fit guides, as are provided on diapers as marketed by The Procter & Gamble Company under the tradename PAMPERS, are applied to the backsheet 5 or to the landing surface 18 for the user to symmetrically place the tape tabs onto the diaper and hence allow proper fastening of the diaper around the baby. For a good fit, it is not only important that the tape tabs 21, 23 are fastened in the right position along the transverse length of the absorbent article 1 of FIG. 1 (in the direction of the short sides), but also that an accurate position of the tape tabs is obtained along the longitudinal sides of the absorbent article. The latter is facilitated by tape tabs 93 which have a symmetrical appearance relative to their centerline.

In FIG. 5, three neighboring tape tabs 105, 107 and 109 are shown prior to being cut from a unitary strip of material 121 (having longitudinal sides 118, 119) to form individual tape tabs. The curved transverse cut lines 120 form, after doubling over of side extensions 110, rounded corners 108. The fold line 111 of the tape tab 107 extends at an angle of 45° relative to the longitudinal sides 98, 99 of the tape tab. The side extension 110 is doubled back onto the adhesive surface of the tape tab 107 and forms at the user's end 101 a gripping part by which the tape 107 can be gripped by a user to be lifted from its release surface and to be attached to the reinforced landing surface as shown in FIG. 1 under reference numeral 18. The fold line 111 can be formed by a creaser 65, 67, as described in FIG. 2, or can alternatively be formed by a number of perforations which extend through the surface of the fastening member of the tape tab 107. The direction of transport of the unitary strip 52 from which the tape tabs 105, 107 and 109 are formed, is indicated in FIG. 5 under T.

FIG. 6 shows a cross-sectional view of the tape tab of FIG. 4 along the line I—I. As shown in FIG. 6, the release member 106, which is formed from release strip 81, is located at the back of the composite tape tab 93 and is placed against the user's end 101 of the fastening member 104. The user's end 101 and the manufacturer's end 103 of the fastening member 104 of the tape tab 93 are formed from a single, homogeneous strip of material, which is a transversely cut-off part of the unitary strip of material 52 in FIGS. 2 and 3.

The release member 106 comprises a crease line 123 along which the lower part of the release member is doubled over. The lower surface 117 of the release member 106 is coated with an adhesive for attachment to the topsheet of an absorbent article. The lower surface 114 of the fastening member 104 is coated with for instance a pressure sensitive adhesive. As the adhesively coated, doubled-over lower part 122 of the release member 106 contacts the adhesive surface 114 of the fastening member 104, the doubled over part 122 of the release member 106 is permanently attached to the fastening member 104.

The upper surface 112 of the release member 106 is for instance silicone-coated to easily detach from the adhesive surface 114 of the fastening member 104. As no adhesive is present between the side extension 94 and the release member 106, the fastening member 104 can be easily separated from the release member 106 at the position of the side extension 94.

FIG. 7 shows the tape tab 93 in accordance with the invention when it is attached to the topsheet 115 and backsheet 116 of a diaper, before use of the diaper. The manufacturer's end of the fastening member 104 is adhesively attached to the backsheet 116 with a relatively aggressive adhesive, that has preferably been pre-applied to the surface 114 of the fastening member. The release member 106 is with its surface 117 adhesively attached to the topsheet 115 of the diaper.

Upon application of the diaper on the wearer, the user's end 101 of the attachment member 104 is peeled from the release surface 112 in the direction of the arrow P, by lifting it by its doubled over side extension 94, which forms a reinforced gripping part. When the fastening member 104 of the composite tape tab 93 is detached from the release surface 112 of the release member 106 up to the position of the lower part 122, further detachment of the fastening member is prevented by the stronger adhesion between the fastening member 104 and the release member 106 at the doubled-over end 122. When, upon detachment of the fastening member 104 by the user, the crease line 123 is reached, the doubled-over part 122 unfolds by hinging backwards along the crease line 123 such that tearing off of the user's end 101 of the fastening member 104 by excessive pull force is prevented.

FIG. 8 shows a further embodiment of a method of manufacturing tape tabs having rounded corners 136 at a user's end 130, in accordance with the invention. A unitary strip of material 129 having longitudinal edges 133 and 134, is transported in the direction indicated by arrow T. The strip 129 is cut along curved transverse cut lines 135, which are regularly spaced apart along the longitudinal edge 133 of the strip 129. Each time, two curved cut lines 135 define cut-out sections 137 which are located at the user's end 130 of the tape tabs. The user's end 130 and the manufacturer's end 131 of the tape tabs are separated by a fold line 141.

The cut-out sections 137 are doubled over onto the strip 129. In FIG. 8, the cut-out sections 137 have, before being folded over onto the strip 129, been indicated by dotted lines. The cut-out sections 137 remain attached to the unitary strip of material 129. When the cut lines 135 are formed, the strip 129 is also provided with crease or fold lines 138. The fold lines 138 are in this embodiment generally parallel to the longitudinal edges of the strip 129.

After cutting the transverse cut lines 135, the cut-out sections 137 are folded toward the center of the strip 129 along fold lines 138. After folding over of the cut-out sections 137, the individual tape tabs 150 are formed by cutting the unitary strip 129 along parallel cut lines 139, which run from the lower edge 134 of the strip 129 to the fold lines 138 and which cut through the doubled-over cut-out sections 137.

The user's end 130 of the tape tabs comprises an adhesive free area 140, by which the tape tabs can be lifted from the release member by the user. Although no reinforced gripping part is formed by doubled over cut-out sections 137, the advantage of this embodiments is that two rounded corners are formed at the user's end and that no scrap is produced.

FIG. 9 shows an embodiment of a method of manufacturing tape tabs 150 having two rounded corners 136 at a user's end 130, in which the cut-out sections 137 along the longitudinal edge 133 of the tape tabs are defined by two curved cut lines and one vertical cut line. The fold lines 138, along which the cut-out sections 137 are doubled over, are placed at a 45° angle with respect to the transverse cut lines 139. Cutout sections 142, 143 are folded along fold lines 138 in the direction of arrows F, to positions 142' and 143' respectively. A symmetrical tape tab is obtained by this method having a fully rounded user's end and having a reinforced gripping part.

For easy detachment of the fastening member of the tape tabs from the release member, the areas 140 can be free of adhesive, or the adhesive of areas 140 can be de-activated for instance by the application of talcum powder.

Figure 10:
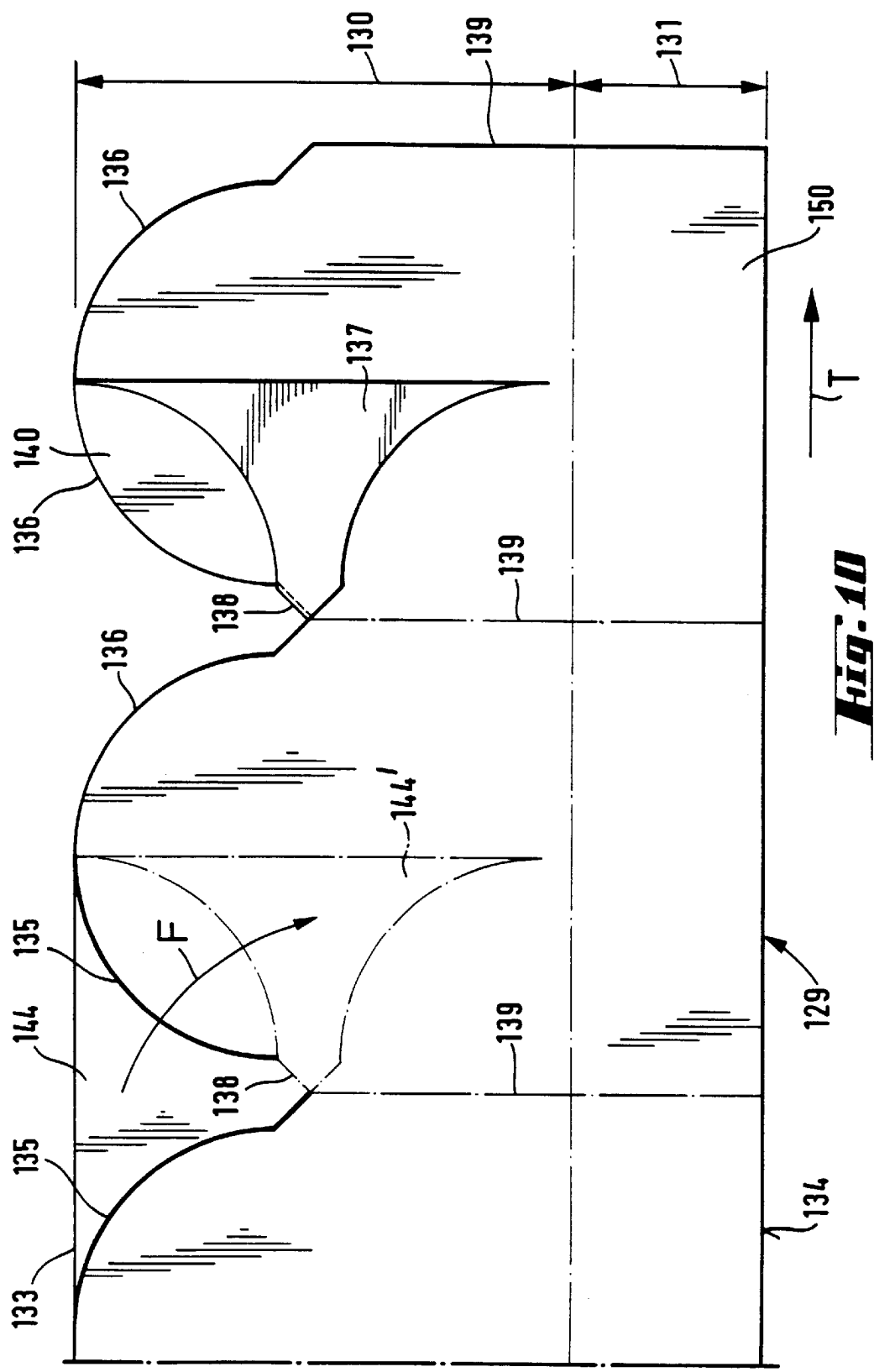

FIG. 10 shows another embodiment of the method according to the invention in which the cut-out sections 137, 144 are folded along 45° fold lines 138, the cut-out section being defined by two curved cut lines. The cut-out sections 137, 144 are folded back onto a single tape tab and is not cut by the transverse cut lines 139. A reinforced gripping part is formed by the doubled-over cut out sections 137, 144 at the user's end 130 of the tape tabs 150.

Preferably, the part of the cut-out sections 137, 144 that is located at the top of the tape tabs, remains attached to the tape tabs. Thereto, the cut lines 135 do not continue all the way up to the center line of each tape tab.

What is claimed is:

1. A method of manufacturing a tape tab for use in a disposable absorbent article, the tape tab having a generally longitudinal shape and comprising a user's end which has a doubled-over gripping part, wherein the method comprises the steps of:

a. cutting a unitary strip of material along parallel, spaced apart curved transverse cut lines, wherein the unitary strip of material comprises two longitudinal edges, the curved transverse cut lines extending from the first longitudinal edge in the direction of the second longitudinal edge, each said curved transverse cut line forming the contour of a round corner of the user's end of a first tape tab and forming a side extension of the user's end of a second tape tab which is adjacent the first tape tab, b. doubling over of each said side extension onto itself along a fold line to form the gripping part, the fold line and the rounded corner forming an indented edge, the indented edge lying laterally inboard of the first longitudinal edge; and c. cutting the unitary strip of material along a second transverse cut line which extends from the indented edge to the second longitudinal edge to form the tape tab.

2. A method of manufacturing a tape tab for use in a disposable absorbent article, the tape tab having a generally longitudinal shape and comprising a rounded user's end, wherein the method comprises the steps of:

a. cutting a unitary strip of material along curved transverse cut lines, wherein the unitary strip of material comprises two longitudinal edges, the curved transverse cut lines extending from the first longitudinal edge in the direction of the second longitudinal edge, each said curved transverse cut line forming the contour of a rounded corner of the user's end, wherein the curved transverse cut lines form a number of regularly spaced-apart partially cut-out sections;

b. doubling over of each said partially cut-out section onto the unitary strip of material along a fold line, the fold line and the rounded corner forming an indented edge, the indented edge lying laterally inboard of the first longitudinal edge; and c. cutting the unitary strip of material along a second transverse cut line which extends from the indented edge to the second longitudinal edge to form the tape tab.

3. A method according to claim 2 wherein the doubled-over partially cut-out section forms a reinforced gripping part at the user's end of the tape tab.

4. A method according to claim 1 wherein one surface of the unitary strip of material is provided with an adhesive, which said surface after forming of the curved transverse cut lines, is covered with a unitary release strip, the unitary strip of material and the release strip forming, after the step of cutting along the second transverse cut line, a composite tape tab comprising a fastening member and a release member.

5. The method according to claim 4 wherein the width of the release strip is substantially equal to the width of the strip of unitary material.

6. The method according to claim 4 wherein the release strip comprises a longitudinally extending release surface for releasable attachment to the tape tab and, adjacent to the release surface, a longitudinally extending fastening surface for permanent attachment to the tape tab.

7. The method according to claim 4 wherein the fold-lines comprise a curved cut-through section and a straight-line fold section to form a second rounded corner at the user's end of the tape tab.

8. The method according to claim 1 wherein the fold lines are formed by a crease line or a line of perforations.

9. The method according to claim 1 wherein one surface of the unitary strip of material is coated with adhesive prior to doubling over of the side extensions, the doubled-over side extensions being attached to the coated surface.

10. A tape tab for use in an absorbent article, the tape tab having a generally longitudinal shape and comprising a fastening member which at a user's end forms a doubled-over gripping part, the fastening member comprising in its flattened state, two longitudinal sides which extend in a generally parallel direction, the first longitudinal side forming a rounded corner at the user's end and the second longitudinal side forming a side extension, the side extension being doubled-over to form the gripping part.

11. A tape tab for use in an absorbent article, the tape tab having a generally longitudinal shape and comprising a fastening member having two longitudinal sides, the fastening member comprising a user's end having two rounded corners, the fastening member comprising along at least one longitudinal side, near the user's end, a doubled-over side extension which side extension, in the flattened state, is disposed on the user's end of the tape tab.

12. An absorbent article comprising a tape tab according to claim 11.

13. An absorbent article comprising a tape tab according to claim 10.

14. A method of manufacturing a tape tab for use in a disposable absorbent article, the tape tabs having a generally longitudinal shape and comprising a rounded user's end, wherein the method comprises the steps of:

a. cutting a unitary strip of material along two curved transverse cut lines and a first substantially straight transverse cut line, wherein:
the unitary strip of material comprises first and second longitudinal edges,
the curved transverse cut lines and the substantially straight transverse cut line extend from the first longitudinal edge in the direction of the second longitudinal edge, each said curved transverse cut line forming a contour of a rounded corner of the user's end, and
the curved transverse cut lines and the substantially straight transverse cut line cooperating to form a pair of longitudinally opposed regularly spaced-apart partially cut-out sections, b. doubling over one of said partially cut-out sections onto the unitary strip of material along a first fold line and the other one of said partially cut-out sections along a second fold line, the fold lines and the rounded corners forming an indented edge, and c. cutting the unitary strip of material along a second transverse cut line which extends from the indented edge to the second longitudinal edge to form the tape tab.

15. An absorbent article comprising a tape tab according to claim 14.

* * * * *